United States Patent [19]
Walker

[11] Patent Number: 5,550,025
[45] Date of Patent: Aug. 27, 1996

[54] DETECTION OF HYDROPHOBIC AMPLIFICATION PRODUCTS BY EXTRACTION INTO AN ORGANIC PHASE

[75] Inventor: G. Terrance Walker, Chapel Hill, N.C.

[73] Assignee: Becton, Dickinson and Company, Franklin Lakes, N.J.

[21] Appl. No.: 503,964

[22] Filed: Jul. 19, 1995

[51] Int. Cl.$^6$ .............................. C12Q 1/68; C12P 19/34; C07H 21/04
[52] U.S. Cl. .............................. 435/6; 435/91.2; 536/24.3
[58] Field of Search .............................. 435/6, 91.2, 91.1

[56] References Cited

FOREIGN PATENT DOCUMENTS

WO90/10064  9/1990  WIPO.

OTHER PUBLICATIONS

P. M. Holland et al. "Detection of Specific Polymerase Chain Reaction Product by utilizing the 5'-3' Exonuclease Activity of Thermus aquaticus DNA Polymerase" *Clin. Chem.* 38:462–463 (1992).

D. Y. Kwoh et al. "Transcription–based amplification system and detection of amplified human immunodeficiency virus type 1 with a bead–based sandwich hybridization format" *Proc. Natl. Acad. Sci. USA* 86:1173–1177 (1989).

P. M. Lizardi et al. "Exponential Amplification of Recombinant–RNA Hybridization Probes" *Bio/Technology* 6:1197–1202 (1988).

R. K. Saiki et al. "Enzymatic Amplification of β–Globin Genomic Sequences and Restriction Site Analysis for Diagnosis of Sickle Cell Anemia" *Science* 230:1350–1354 (1985).

J. C. Guatelli, et al. "Isothermal, in vitro amplification of nucleic acids by a multienzyme reaction modeled after retroviral replication" *Proc. Natl. Acad. Sci. USA* 87:1874–1878 (1990).

G. T. Walker, et al. "Strand displacement amplification—an isothermal, in vitro DNA amplification technique" *Nucl. Acids Res.* 20:1691–1696 (1992).

G. T. Walker et al. "Isothermal in vitro amplification of DNA by a restriction enzyme/DNA polymerase system" *Proc. Natl. Acad. Sci. USA* 89:392–296 (1992).

*Primary Examiner*—Stephanie W. Zitomer
*Assistant Examiner*—Amy Atzel
*Attorney, Agent, or Firm*—Donna R. Fugit

[57] ABSTRACT

Amplification of a target sequence is detected qualitatively or quantitatively by concurrent generation of secondary amplification products labeled with a lipophilic label. The secondary amplification products are designed such that they are generated and cleaved or nicked in a target amplification-dependent manner. This reduces the number of hydrophilic nucleotides linked to the lipophilic label and allows the cleaved or nicked secondary amplification product comprising the lipophilic label to be transferred from the aqueous reaction phase to an organic phase for detection as an indicator of target amplification.

20 Claims, 2 Drawing Sheets

SEQUENCE LISTING ( 1 ) GENERAL INFORMATION:

( i i i ) NUMBER OF SEQUENCES: 7

( 2 ) INFORMATION FOR SEQ ID NO:1:

( i ) SEQUENCE CHARACTERISTICS:
        ( A ) LENGTH: 33 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:1:

GGAATTCATC CGTATGGTGG ATAACGTCTT TCA        33

( 2 ) INFORMATION FOR SEQ ID NO:2:

( i ) SEQUENCE CHARACTERISTICS:
        ( A ) LENGTH: 41 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:2:

GCTCGAGTTG TCTACATCCG TATGGTGGAT AACGTCTTTC A        41

( 2 ) INFORMATION FOR SEQ ID NO:3:

( i ) SEQUENCE CHARACTERISTICS:
        ( A ) LENGTH: 40 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:3:

CGATTCCGCT CCAGACTTCT CGGGTGTACT GAGATCCCCT        40

( 2 ) INFORMATION FOR SEQ ID NO:4:

( i ) SEQUENCE CHARACTERISTICS:
        ( A ) LENGTH: 40 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:4:

ACCGCATCGA ATGCATGTCT CGGGTAAGGC GTACTCGACC        40

( 2 ) INFORMATION FOR SEQ ID NO:5:

( i ) SEQUENCE CHARACTERISTICS:
        ( A ) LENGTH: 13 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:5:

CGCTGAACCG GAT                                                                             13

( 2 ) INFORMATION FOR SEQ ID NO:6:

( i ) SEQUENCE CHARACTERISTICS:
        ( A ) LENGTH: 13 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:6:

TGGACCCGCC AAC                                                                             13

( 2 ) INFORMATION FOR SEQ ID NO:7:

( i ) SEQUENCE CHARACTERISTICS:
        ( A ) LENGTH: 33 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:7:

GGAATTCATC CGTATGGTGG ATAACGTCTT TCA                     33

DETECTION OF HYDROPHOBIC AMPLIFICATION PRODUCTS BY EXTRACTION INTO AN ORGANIC PHASE

FIELD OF THE INVENTION

The invention relates to detection of nucleic acid amplification and in particular to detection of nucleic acid amplification by concurrent generation of secondary amplification products.

BACKGROUND OF THE INVENTION

In vitro nucleic acid amplification techniques provide powerful tools for detection and analysis of small amounts of nucleic acids. The extreme sensitivity of such methods has lead to attempts to develop them for diagnosis of infectious and genetic diseases, isolation of genes for analysis, and detection of specific nucleic acids as in forensic medicine. Nucleic acid amplification techniques can be grouped according to the temperature requirements of the procedure. The polymerase chain reaction (PCR; R. K. Saiki, et al. 1985. *Science* 230, 1350–1354), ligase chain reaction (LCR; D. Y. Wu, et al. 1989. *Genomics* 4, 560–569; K. Barringer, et al. 1990. *Gene* 89, 117–122; F. Barany. 1991. *Proc. Natl. Acad. Sci. U.S.A.* 88, 189–193) and transcription-based amplification (D. Y. Kwoh, et al. 1989. *Proc. Natl. Acad. Sci. U.S.A.* 86, 1173–1177) require temperature cycling. In contrast, methods such as Strand Displacement Amplification (SDA; G. T. Walker, et al. 1992. *Proc. Natl. Acad. Sci. U.S.A.* 89, 392–396; G. T. Walker, et al. 1992. *Nuc. Acids. Res.* 20, 1691–1696; U.S. Pat. No. 5,270,184), self-sustained sequence replication (3SR; J. C. Guatelli, et al. 1990. *Proc. Natl. Acad. Sci. U.S.A.* 87, 1874–1878) and the Qβ replicase system (P. M. Lizardi, et al. 1988. *BioTechnology* 6, 1197–1202) are isothermal reactions. In addition, WO 90/10064 and WO 91/03573 describe use of the bacteriophage phi29 replication origin for isothermal replication of nucleic acids.

A variety of methods have been developed to detect and/or measure nucleic acid amplification. For the most part, these methods are primer-based, meaning that they depend on hybridization of a primer to the target sequence, in some cases followed by extension of the primer. Primer-based detection of amplified nucleic acids in PCR often relies on incorporation of an amplification primer into the amplified product (amplicon) during the amplification reaction. Features engineered into the PCR amplification primer therefore appear in the amplification product and can be used either to detect the amplified target sequence or to immobilize the amplicon for detection by other means. However, primer-based methods of detecting PCR amplification products require two amplification reactions to achieve high sensitivity, i.e., detection of fewer than 100 copies of the target sequence. That is, a first amplification of the target sequence is followed by a second amplification using nested primers incorporating the desired modifications for capture and/or detection. Two consecutive amplifications are needed to avoid unacceptably high levels of background signal produced by amplification of non-target DNA spuriously primed with the modified, signal-generating primers. This feature of the prior art methods makes them time-consuming and cumbersome, and the advantages of primer-based detection methods are therefore often offset by the requirement for a second consecutive amplification reaction.

P. M. Holland, et al. (1992. *Clin. Chem.* 38, 462–463) describe a method for detecting amplification products of PCR in which the 5'–3' exonuclease activity of Taq DNA polymerase is used to generate target amplification-specific signal by digestion of a labeled probe hybridized downstream of the amplification primer. The labeled probe is not extendable, possibly because certain of the detection systems described make use of a 3' end-label. Further, an extendable labeled probe would function as a PCR amplification primer, thereby increasing non-specific background signal in the reaction. Cleaved probe fragments are generated during amplification, and may be differentiated from uncleaved probe in a variety of ways, depending on the type of probe label. The authors suggest thin-layer chromatography or capture by a 3' biotin label to separate cleaved from uncleaved probe, or sequencing. These detection methods require cumbersome and time consuming manipulations of the sample after amplification. The present methods for primer-based detection of target amplification also make use of a single amplification reaction to concurrently generate secondary products for detection. In contrast to P. M. Holland, et al. and other prior art methods, however, the secondary amplification products are detected in a simple format by extraction into an organic phase.

As used herein, the following terms and phrases are defined as follows:

An amplification primer is a primer for amplification of a target sequence by primer extension. For SDA, the 3' end of the amplification primer (the target binding sequence) hybridizes at the 3' end of the target sequence. The amplification primer comprises a recognition site for a restriction endonuclease near its 5' end. The recognition site is for a restriction endonuclease which will cleave one strand of a DNA duplex when the recognition site is hemimodified ("nicking"), as described by Walker, et al. (1992. *PNAS*, supra). A hemimodified recognition site is a double stranded recognition site for a restriction endonuclease in which one strand contains at least one derivatized nucleotide which causes the restriction endonuclease to nick the primer strand rather than cleave both strands of the recognition site. Usually, the primer strand of the hemimodified recognition site does not contain derivatized nucleotides and is nicked by the restriction endonuclease. Alternatively, the primer may contain derivatized nucleotides which cause the unmodified target strand to be protected from cleavage while the modified primer strand is nicked. Such restriction endonucleases can be identified in routine screening systems in which a derivatized dNTP is incorporated into a restriction endonuclease recognition site for the enzyme. The preferred hemimodified recognition sites are hemiphosphorothioated recognition sites for the restriction endonucleases HincII, HindII, AvaI, NciI, Fnu4HI, BsoBI and BsrI. The amplification primer also comprises a 3'—OH group which is extendable by DNA polymerase when the target binding sequence of the amplification primer is hybridized to the target sequence. For the majority of the SDA reaction, the amplification primer is responsible for exponential amplification of the target sequence. As no special sequences or structures are required, amplification primers for PCR generally consist only of target binding sequences.

Extension products are nucleic acids which comprise a primer and a newly synthesized strand which is the complement of the target sequence downstream of the primer binding site. Extension products result from hybridization of a primer to a target sequence and extension of the primer by polymerase using the target sequence as a template.

A bumper primer is a primer which anneals to a target sequence upstream of the amplification primer, such that extension of the bumper primer displaces the downstream amplification primer and its extension product. Extension of bumper primers is one method for displacing the extension products of amplification primers, but heating is also suitable.

The terms target or target sequence refer to nucleic acid sequences to be amplified. These include the original nucleic acid sequence to be amplified, its complementary second strand and either strand of a copy of the original sequence which is produced in the amplification reaction. The target sequence may also be referred to as a template for extension of hybridized primers.

A signal primer is a primer which hybridizes to a target sequence downstream of an amplification primer such that extension of the amplification primer displaces the signal primer, a portion of the signal primer or the signal primer extension product. The signal primer further comprises a lipophilic reporter group or label which facilitates detection of secondary amplification products generated from the signal primer.

Amplification products, amplified products or amplicons are copies of the target sequence generated by hybridization and extension of an amplification primer. This term refers to both single stranded and double stranded amplification primer extension products which contain a copy of the original target sequence, including intermediates of the amplification reaction.

Secondary amplification products or secondary products are oligonucleotides generated from a signal primer in a target amplification-dependent manner. These terms refer to single stranded or double stranded products generated from signal primers, as well as portions of signal primers or signal primer extension products generated as a result of target amplification.

Cleavage of an oligonucleotide refers to breaking the phosphodiester bonds of the molecule such that two oligonucleotide cleavage products are produced, i.e., breaking the bonds of both strands of a DNA duplex or breaking the bond of single-stranded DNA. This is in contrast to nicking, which refers to breaking the phosphodiester bond of only one of the two strands in a DNA duplex.

SUMMARY OF THE INVENTION

The present invention provides methods for detecting amplification of a target sequence. Secondary, target-specific amplification products are generated from signal primers in a reaction which is coupled to target amplification. The secondary amplification products can therefore be used to detect and/or measure target sequence amplification. The secondary amplification product is an oligonucleotide which comprises a lipophilic label. The labeled secondary amplification product is designed such that it is cleaved or nicked in a target amplification-dependent manner during amplification, thereby reducing the number of hydrophilic nucleotides linked to the lipophilic label and allowing the labeled cleavage product to be transferred from the aqueous phase of the amplification reaction into an organic phase. The more hydrophilic uncleaved or unnicked signal primer remains in the aqueous phase as a result of the greater number of hydrophilic nucleotides linked to the lipophilic label. The label transferred to the organic phase is detected as an indicator of target amplification. Detection of the label may be a qualitative or quantitative measure of amplification of a target sequence. The inventive methods are especially useful for monitoring amplification reactions in situations where direct detection of target sequence amplicons would interfere with further manipulations or procedures. Organic extraction for detection of the secondary amplification products provides a highly sensitive detection system in a procedurally simple and rapid format.

DETAILED DESCRIPTION OF THE INVENTION

Figure 1:
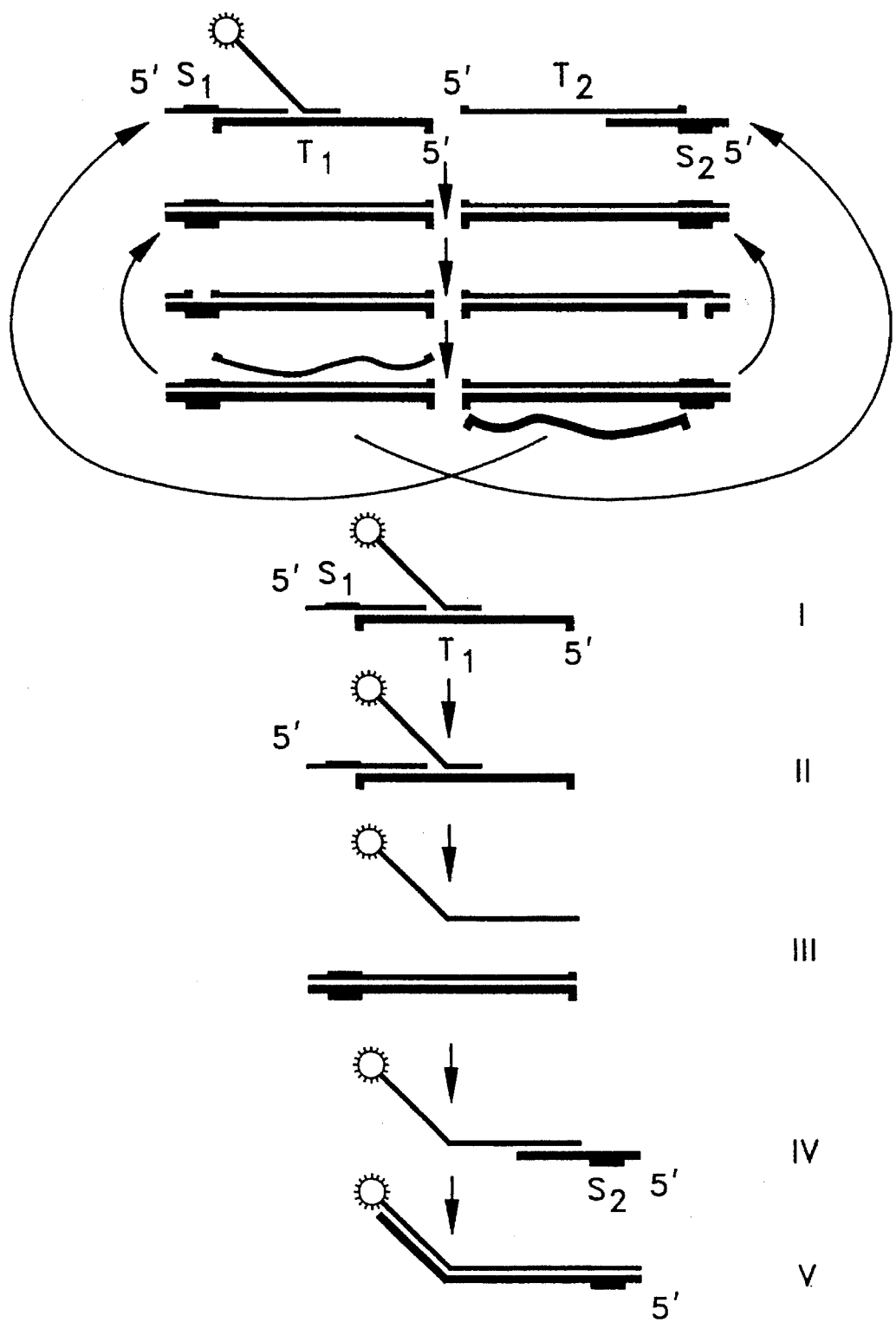
FIG. 1 illustrates generation of a secondary amplification product concurrently with target amplification by SDA.

The present invention is a method for detecting or monitoring amplification of a target by conversion of a hydrophilic signal primer comprising a lipophilic label to a lipophilic secondary amplification product which is transferred from the aqueous reaction phase to an organic phase for detection. Conversion takes place in a target amplification-dependent manner. That is, production of the secondary amplification product is coupled to amplification of the target sequence. Further, the secondary amplification product is generated concurrently with amplification of the target sequence. Once generated, the secondary amplification product does not interfere with or inhibit normal amplification of the desired target sequence. The methods are therefore especially useful for detecting amplification of the target sequence in situations where direct detection of the amplified target sequence itself would inhibit or prevent further reaction or manipulation of the amplicons. The lipophilic properties of the secondary amplification product allow simple separation from unreacted, labeled signal primers, e.g., by transfer to an organic phase.

In one embodiment of the invention, amplification primers for SDA are hybridized to a target sequence which is then amplified generally as described by Walker, et al. (1992. *PNAS* or 1992 *Nuc. Acids Res.*, supra). As described in these two publications, the target sequence may be prepared for SDA either by restricting total DNA with an appropriate restriction endonuclease (e.g., RsaI) or by generating target fragments having the appropriate restriction endonuclease recognition sites at the ends using bumper primers and amplification primers. Prepared fragments containing the target sequence are then amplified by SDA. However, the SDA reaction of the invention further comprises at least one signal primer which results in simultaneous or concurrent generation of a secondary amplification product for use in detecting or monitoring amplification of the target sequence. For certain applications, it may be preferable to include a pair of signal primers, each of which hybridizes to one of the two strands of a double-stranded target sequence. The signal primer hybridizes to the target sequence downstream of the hybridization site of the amplification primer. It may be extended by polymerase in a manner similar to extension of the amplification primers, but this feature is not required in all amplification systems (for example the PCR method of Example 4). That is, the signal primer hybridizes at a site within the target sequence such that extension of the amplification primer displaces the signal primer, a portion of the signal primer or the signal primer extension product. At least the 3' end of the signal primer comprises a sequence which hybridizes to the target sequence. Alternatively, the entire signal primer may hybridize to the target sequence, depending on the method selected for reducing the number of nucleotides in the signal primer The signal pruner is further labeled at its 5' end with a lipophilic label. The lipophilic label becomes incorporated into the secondary amplification product as a result of target amplification. In this embodiment, the signal primers cannot function as amplification primers in the SDA reaction because they lack a nickable restriction endonuclease recognition site. Consequently, any extension products formed through errant extension of a signal primer on a non-target template cannot undergo subsequent amplification. Because mispriming itself is comparatively rare, it is generally detectable only after subsequent amplification of the misprimed sequence. Therefore, in the absence of subsequent amplification, the signal primers may be present in the amplification reaction with no significant increase in background signal levels This, in conjunction with simple organic extraction to separate labeled secondary amplification products for analysis, greatly simplifies the procedure.

Generation of a double-stranded secondary amplification product during SDA is illustrated in FIG. 1. The top portion of FIG. 1 illustrates the amplification reaction occuring in SDA. As stated above, nucleic acid fragments having appropriate restriction endonuclease recognition sequences at the ends and containing the target sequence may be prepared for SDA either as described by Walker, et al. 1992. *PNAS*, supra or as described by Walker, et al. 1992 *Nuc. Acids Res.*, supra. For simplicity, the illustrations in FIGS. 1 and 2 begin with an amplifiable nucleic acid fragment containing the target sequence. If prepared according to Walker, et al. 1992. *PNAS*, supra, it represents restricted double stranded DNA which has been denatured. If prepared according to Walker, et al. 1992. *Nuc. Acids Res.*, supra, appropriate restriction endonuclease recognition sites are added to the fragment according to the disclosed target generation scheme. During SDA target generation, the bumper, amplification and signal primers hybridize to a target sequence in the target generation scheme, with extension of each upstream primer displacing the downstream primer and concurrently generating amplifiable target fragments and secondary amplification products.

The bottom portion of FIG. 1 illustrates the concurrent conversion of the single-stranded signal primer to double-stranded form. A signal primer hybridizes to one strand of the target sequence downstream of an amplification primer (I). Both the amplification primer and the signal primer are extended by DNA polymerase using the target sequence as a template (II). The signal primer extension product is displaced from the template by extension of the amplification primer and in turn serves as a template for hybridization and extension of a second amplification primer (III and IV), rendering the signal primer extension product double-stranded (V). A second signal primer which hybridizes to the second strand of a double stranded target sequence may optionally be included in the reaction. The second signal primer hybridizes to the second strand of the target sequence downstream of the second amplification primer and is extended and displaced by extension of the second amplification primer. The second signal primer extension product is rendered double stranded by hybridization and extension of the first amplification primer. It will also be apparent from the illustration of the invention in FIG. 1 that multiple signal primers may be employed, each hybridizing to the target sequence downstream of the other on the same strand, and all signal primers being hybridized downstream of the amplification primer. In this manner, each signal primer is displaced by extension of the upstream signal primer and the most 5' signal primer is displaced by the amplification primer. The multiple signal primers should be designed so that they do not hybridize to each other or to the amplification primer for the opposite strand of the target sequence. Use of multiple signal primers has the advantage of increasing or amplifying the signal generated per target, with an increase in sensitivity of the assay, The number of nucleotides linked to the lipophilic label in the double stranded secondary amplification product is reduced in a target amplification-dependent manner to facilitate organic extraction and detection of the label. That is, unreacted, single stranded signal primer molecules with the linked label are prevented from entering the organic phase by their greater number of linked nucleotides, which give the molecule more hydrophilic properties. In one embodiment, the signal primer comprises a restriction endonuclease recognition site placed such that cleavage or nicking of the double-stranded secondary amplification product by the restriction endonuclease generates a labeled fragment comprising a reduced number of nucleotides which is sufficiently lipophilic to be transferred from the aqueous amplification reaction to an organic phase. This recognition site should be for a restriction endonuclease which does not cleave the target sequence. Typically, such a restriction endonuclease recognition site will be placed toward the 5' end of the signal primer to minimize the number of nucleotides remaining linked to the label after cleavage or nicking. The restriction endonuclease does not cleave its recognition site in the single stranded signal primer. However, the signal primer becomes cleavable or nickable by the restriction endonuclease when convened from single- to double-stranded form during target amplification. Therefore, only double-stranded secondary amplification products produced during target amplification will be cleaved or nicked and transferred to the organic phase.

Figure 2:
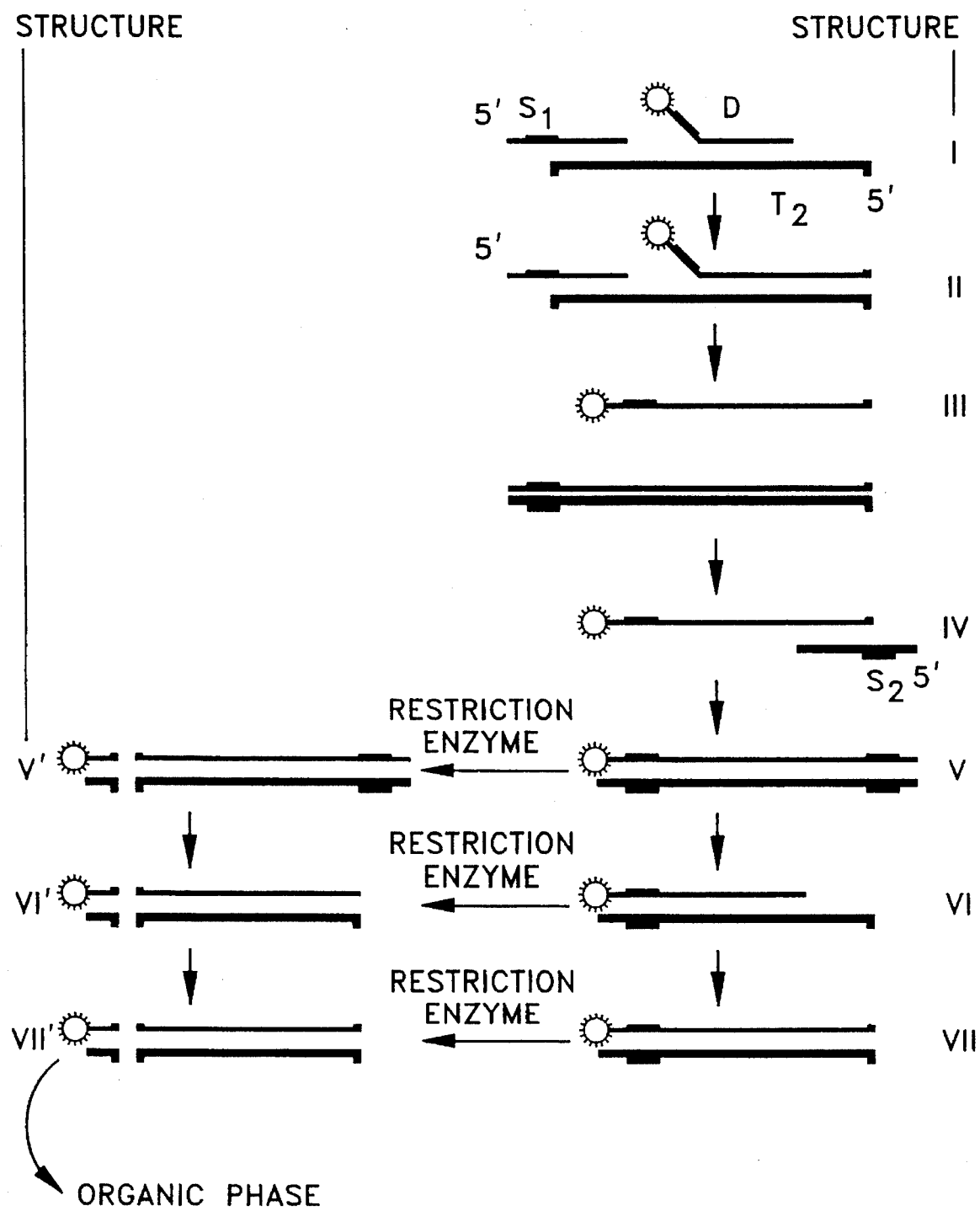
FIG. 2 illustrates generation of a secondary amplification product concurrently with SDA, the secondary product comprising a restriction endonuclease recognition site which is cleaved to release a lipophilic cleavage product.

The reaction in which a restriction endonuclease recognition site is cleaved is illustrated in FIG. 2, where the restriction endonuclease recognition site is shown as a raised portion on the nucleic acid strand. The initial steps for generation of the double-stranded secondary amplification product from the single-stranded signal primer (structures I–V) are those illustrated in FIG. 1 (I–V). FIG. 2 illustrates a double-stranded restriction endonuclease recognition site in structure V (raised blocks) which is cleavable by the restriction endonuclease to generate two cleavage products—a lipophilic cleavage product and an unlabeled oligonucleotide cleavage product. In addition, the restriction endonuclease recognition site at the 5' end of the extended $S_2$ primer in structure V is nickable and can be displaced, producing a strand to which the signal primer can hybridize (VI). The double stranded restriction endonuclease recognition site in VI may also be cleaved to generate a labeled lipophilic cleavage product (VI'), or it may be extended by polymerase to generate a fully double-stranded molecule (VII) prior to cleavage and generation of the labeled lipophilic cleavage product (VII'). V', VI' and VII' represent alternative reaction pathways for generation of labeled lipophilic secondary amplification products. As illustrated, the recognition site becomes double stranded during target amplification and is cleaved by the restriction endonuclease, releasing a secondary amplification cleavage product comprising the lipophilic label linked to fewer hydrophilic nucleotides than are present in the signal primer. As a result of its increased hydrophobicity and increased lipophilicity, the labeled cleavage product becomes soluble in the organic phase, separating label generated as a result of target amplification from the label of the unreacted signal primer. When very few nucleotides remain linked to the label, the double-stranded secondary amplification cleavage product may denature into single strands. This is also the case for nicked secondary amplification products, as described below. Longer secondary amplification cleavage products may be sufficiently stable to remain hybridized. Whether the cleavage product is single- or double-stranded is not critical to the invention, as either form will be transferrable to the organic phase on the basis of increased lipophilicity. Unreacted full-length signal primer, which is more hydrophilic due to the greater number of hydrophilic nucleotides linked to the lipophilic label, remains in the aqueous phase. Therefore, if there is no target amplification, little or no label will be detected in the organic phase. As greater levels of target amplification occur, more label will be detected in the organic phase. The methods of the invention may therefore be used for either qualitative detection of amplification (presence or absence of target) or for quantitation of amplification (measuring the amount of label in the organic phase to determine the initial amount of target).

When amplification is by SDA, the restriction endonuclease used to reduce the number of nucleotides linked to the lipophilic label may be the same restriction endonuclease employed in the SDA reaction (e.g., BsoBI or HincII). In this case, the restriction endonuclease recognition site in the signal primer may be an alternative recognition site for the restriction endonuclease which is not protected from double stranded cleavage by incorporation of modified dNTPs during amplification. The restriction endonuclease recognition site in the amplification primers, however, is a recognition site which is nicked by the restriction endonuclease when in hemimodified form. For example, the HincII recognition site GTCGAC undergoes double stranded cleavage by HincII even when hemimodified by incorporation of α thio-dATP. This recognition site is therefore suitable for use in the signal primer. In contrast, the HincII recognition site GTTGAC is nicked when hemimodified by incorporation of αthio-dATP and is therefore suitable for use in the amplification primers. Similarly, the BsoBI recognition site CTCGAG undergoes double stranded cleavage by BsoBI even when hemimodified with αthio-dCTP and is therefore suitable for use in the signal primer. The BsoBI recognition site CTCGGG is nicked when hemimodified with αthio-dCTP and is therefore suitable for use in the amplification primers.

A nickable restriction endonuclease recognition site in the signal primer may also be used to generate the secondary amplification products, as very short labeled nucleotide segments resulting from nicking would not remain hybridized and would be released into the organic phase. If some of the short, labeled, nicked segments remain hybridized to the signal primer, the nick can be placed close to the 5' end of the signal primer to prevent initiation of polymerization and displacement by the polymerase. Polymerases, in general, require about 8–10 nucleotides 5' to the nick for priming. Therefore, using restriction endonucleases such as HincII or BsoBI, the target sequence may be amplified and the number of nucleotides in the secondary amplification products may be concurrently reduced by means of a single restriction endonuclease. Alternatively, the restriction endonuclease for reducing the number of nucleotides in the secondary amplification product may be different from the restriction endonuclease for SDA. For example, an EcoRI recognition site, or any other recognition site which remains cleavable upon incorporation of modified dNTPs during SDA, may be included in the signal primer. In this type of reaction, both the cleaving restriction endonuclease and the nicking restriction endonuclease may be present in the amplification reaction to achieve concurrent amplification of target and generation of lipophilic cleavage products. Routine screening methods testing a restriction endonuclease against its hemimodified recognition site may be used to identify those recognition sites which are cleaved and those which are nicked.

It will be apparent from the reactions illustrated in FIGS. 1 and 2 that, in addition to SDA, the methods of the invention are easily adapted to other primer extension amplification methods (e.g., PCR or 3SR). For example, replacing SDA amplification primers with PCR amplification primers and a PCR DNA polymerase which lacks 5'→3' exonuclease activity (e.g., Sequencing Grade Taq from Promega or exo⁻ Vent or exo⁻ Deep Vent from New England BioLabs) in the reaction scheme of FIG. 2, secondary amplification products are generated which contain a cleavable, double-stranded restriction endonuclease recognition site contributed by the signal primer. As thermocycling is a feature of amplification by PCR, the restriction endonuclease is preferably added at low temperature after the final cycle of primer annealing and extension, however, a thermophilic restriction endonuclease which remains active through the high temperature cycle of the PCR reaction could be present during amplification. As in SDA Systems, cleavage of the restriction endonuclease recognition site generates a lipophilic secondary amplification product. This secondary amplification product can be transferred to an organic phase for detection as an indicator of target amplification as herein described.

In a preferred PCR method according to the invention, lipophilic secondary amplification products may be generated from a hydrophilic signal primer in a target amplification-dependent manner by employing a lipophilic label in the PCR methods of P. M. Holland, et al., supra. Referring to the Figure at page 462 of the publication, Taq DNA polymerase extends the amplification primer and displaces the first few nucleotides of the hybridized downstream probe (i.e., the signal primer), cleaving the signal primer at the phosphodiester bond joining the displaced region with the remaining base-paired portion of the signal primer. This releases a labeled secondary amplification cleavage product with significantly fewer nucleotides linked to the lipophilic label (usually 1–2). This cleavage product is generated in a target amplification-dependent manner (i.e., only upon hybridization and extension of amplification primers and signal primers on a target sequence), as the partially double-stranded "fork" structure is the preferred substrate for cleavage. The lipophilic label with the reduced number of linked nucleotides can then be transferred to an organic phase for detection as an indicator of target amplification. As generation of lipophilic cleavage products in this system does not require that the 5' end of the signal primer be double-stranded, the 3'-end of the signal primer may be unextendable as described by the authors. Alternatively, the 3' end of the signal primer may be extendable without interfering with generation, phase transfer and detection of the lipophilic cleavage product. However, an extendable signal primer may increase background and extending the signal primer unnecessarily reduces the efficiency of the polymerase in amplification. The number of nucleotides linked to a selected lipophilic label can be varied by varying the nucleotide sequence of the signal primer. Higher A+T content in the 5' end of the signal primer facilitates generation of larger, less lipophilic cleavage products as a result of more efficient displacement by Taq polymerase and/or "breathing" of the duplex before cleavage. Conversely, increased G+C content generally reduces the size of the cleavage product and increases its lipophilicity. Such routine variation of the sequence of the signal primer may therefore be used to optimize the length of the cleavage product for a selected label and a selected organic phase. Alternatively, the number of nucleotides linked to the lipophilic label in the cleavage product may be increased by inclusion of a non-hybridizing tail in the signal primer between the lipophilic label and the target binding sequence of the signal primer. However, as previously stated, more lipophilic secondary amplification products having fewer linked nucleotides are generally preferred.

For adaptation of the inventive methods to 3SR, it is only necessary to employ a 5'→3' exonuclease deficient reverse transcriptase with strand displacing activity in the 3SR reaction, with hybridization of a signal primer to the RNA target downstream of the "3' primer" and/or the "5' primer" of Guatelli, et al., supra (see Guatelli's FIG. 1, page 1875). In a reaction scheme similar to Applicant's FIG. 1, the hybridized signal primer containing the restriction endonuclease recognition sequence is 1) extended, and 2) displaced by extension of the upstream DNA primer. The displaced extension product is then made double stranded by hybridization and extension of the other primer. This renders the restriction endonuclease recognition site cleavable, and a lipophilic secondary amplification product is generated for transfer to the organic phase. Also similar to SDA, the signal primer for 3SR does not contain a T7 RNA polymerase promoter sequence and therefore cannot function as an amplification primer, reducing nonspecific background signal.

It will be apparent from the foregoing examples that the essential feature of the invention is generation of a lipophilic secondary amplification product from a hydrophilic signal primer by a target amplification-dependent reduction in the number of nucleotides linked to the lipophilic label. Any such secondary amplification product, regardless of the reaction mechanism by which it is produced during target amplification, will be transferrable to an organic phase as herein described for detection as an indicator of target amplification.

Compounds for use as labels on oligonucleotides are well known in the art, and include dyes, enzymes, radiolabels, ligands, antigens/haptens and antibodies. Any such labels which are lipophilic and detectable upon transfer to the organic phase are suitable for use in the invention. Dyes are particularly useful due to the ease with which they can be detected, and many colorimetric and fluorescent dyes have the necessary lipophilic properties. Examples of such dyes are discussed in *Molecular Probes Handbook of Fluorescent Probes and Research Chemicals*, 5th Edition, by Richard P. Haugland, Molecular Probes Inc. (1992) and *Fluorescent Probes in Cellular and Molecular Biology* by Jan Slavik, CRC Press (1994). Specific lipophilic dyes suitable for use in the invention include, but are not limited to, diphenylhexatriene, Nile Red, N-phenyl-1-naphthylamine, Prodan, Laurodan, Pyrene, Perylene, rhodamine, rhodamine B, tetramethylrhodamine, Texas Red, sulforhodamine, 1,1'-didodecyl-3,3,3',3'tetramethylindocarbocyanine perchlorate, octadecyl rhodamine B and the BODIPY dyes available from Molecular Probes Inc. (e.g., BODIPY 558/568, BODIPY D-3921, BODIPY D-3935, BODIPY D-3933, BODIPY B-3930, BODIPY B-3932, BODIPY B-2192, BODIPY B-2188, BODIPY B-2223, BODIPY B-2226, BODEPY B-2229, and BODIPY B-2185). For a selected lipophilic label, the appropriate number of linked nucleotides in the signal primer to obtain hydrophilic properties and the appropriate number of linked nucleotides in the secondary amplification product to obtain lipophilic properties may be routinely determined using simple screening methods such as those described in Example 1. That is, by linking a variable number of nucleotides to the selected lipophilic label and testing for solubility in an organic phase or an aqueous phase, the practitioner can design a suitable signal primer for use in the methods of the invention. The label associated with the secondary amplification product may then be detected after transfer to the organic phase using methods known in the art appropriate for the selected label. In the case of colorimetric dyes, absorbance of light is typically used for detection, for example using a spectrophotometer. Fluorescent dyes may also be detected by absorbance. Alternatively, fluorescent dyes may be excited by an appropriate wavelength of light and detected by the emission of fluorescence, for example in a fluorometer or by fluorescence spectroscopy.

Similarly, a variety of organic phases may be screened by routine methods to determine solubility of a signal primer or secondary amplification product incorporating a selected label. That is, although different signal primers and secondary amplification products incorporating different lipophlic labels may exhibit different solubility characteristics in different organic phases, whether or not a selected organic phase is useful in the methods of the invention can be determined using simple screening assays such as those described in Example 1. Any organic phase in which the secondary amplification product is soluble and the signal primer is insoluble (or minimally soluble, preferably below the level of detection) is suitable for use in the methods of the invention, e.g., chloroform, phenol, butanol, methylene chloride and mixtures thereof. The proportions of the components in a mixed organic phase are generally not critical, and can be optimized as necessary using simple screening assays as described above. The lipophilic secondary amplification product is typically transferred to the organic phase by mixing the organic phase with the aqueous reaction phase to extract it. The aqueous and organic phases are then separated, naturally or assisted by centrifugation, and any label extracted into the organic phase is detected.

If solubility of the lipophilic secondary amplification product in the organic phase is inadequate to provide the desired sensitivity or if it is otherwise desired to enhance solubility, additives may be included in the aqueous phase to increase its ionic strength. By increasing the ionic strength of the aqueous phase, the solubility of the lipophilic secondary amplification product is reduced. Such additives include compounds which ionize in aqueous solution. Such compounds include, but are not limited to, mineral acids (e.g., phosphoric acid, hydrochloric acid, sulfuric acid), organic acids (e.g., acetic acid and other carboxylic acids), chloride salts (e.g., sodium, potassium, calcium, or magnesium chlorides), carbonate salts (e.g., sodium, potassium, calcium or magnesium carbonate), sulfate salts (e.g., sodium, potassium, calcium or magnesium sulfate) and phosphate salts (e.g., sodium, potassium, calcium or magnesium phosphate). For any selected combination of signal primer, secondary amplification product and organic phase, the amount of the selected additive to be included in the aqueous phase to enhance transfer of the lipophilic secondary amplification product to the organic phase may be determined by routine screening assays in which transfer is monitored in the presence of a range of aqueous phase ionic strengths.

EXAMPLE 1

A series of dye-conjugated oligodeoxynucleotides were screened for their solubility in a variety of organic phases.

Short oligodeoxynucleotides of varying length were synthesized and labeled at the 5'-end with BODIPY 558/568 (Molecular Probes, Inc. catalog #2218) as recommended by the manufacturer:

| | |
|---|---|
| dye-1-mer | 5'-BODIPY-dG |
| dye-2-mer | 5'-BODIPY-dGG |
| dye-3-mer | 5'-BODIPY-dGGA |
| dye-4-mer | 5'-BODIPY-dGGAA |
| dye-33-mer | 5'-BODIPY-dGGAATTCATCCGTATGGTGGATAACGTCTTTCA (SEQ ID NO: 1) |

The labeled oligodeoxynucleotides and the free dye were then tested for their ability to partition from an aqueous phase into each of several organic phases. The oligos or free dye were dissolved in 100 μL of 50 mM $K_2PO_4$, pH 7.5, and an equal volume of organic solvent was added. The samples were mixed by vortexing and the two phases were separated by centrifugation. The amount of BODIPY-oligodeoxynucleotide (or free dye) in each of the two phases was determined by fluorescence spectroscopy. The percentage of BODIPY-oligodeoxynucleotide (or free dye) transferred from the aqueous phase to the organic phase is shown in Table I.

TABLE I

| DYE-OLIGO | CHLOROFORM | BUTANOL | PHENOL/CHLOROFORM (50:50) | METHYLENE CHLORIDE |
|---|---|---|---|---|
| Dye Alone | 92% | 90% | 79% | 81% |
| Dye-1-mer | 18% | 71% | 78% | 5% |
| Dye-2-mer | 5% | 7% | 45% | 7% |
| Dye-3-mer | 5% | 3% | 26% | 5% |
| Dye-4-mer | 3% | 2% | 5% | 4% |
| Dye-33-mer | 6% | 4% | 3% | 10% |

In this experiment, phenol/chloroform was particularly well suited for extracting BODIPY-labeled 1–3-mers. Butanol worked well for extraction of BODIPY-labeled 1-mer. None of the organic phases successfully extracted BODIPY-labeled 33-mer or BODIPY-labeled 4-mer. This screening assay demonstrates that for this dye, a 1, 2, or 3-mer secondary amplification product will be transferred from the aqueous phase to phenol/chloroform (or butanol if the secondary amplification product is a 1-mer). In addition, a signal primer which is at least four nucleotides in length is sufficiently hydrophilic in this system to remain in the aqueous phase.

Various aqueous phase additives were tested in the assay to determine their ability to enhance phenol/chloroform extraction of the dye-3-mer without resulting in extraction of the dye-33-mer. The dye-oligodeoxynucleotides or the free dye were dissolved in 100 μL of 50 mM $K_2PO_4$, pH 7.5 and 10 μL of the indicated acid or salt was added. An equal volume of phenol/chloroform (50:50) was added, and the phases were mixed by vortexing and separated by centrifugation. The amount of BODIPY-oligodeoxynucleotide or free dye in each of the two phases was determined by fluorescence spectroscopy. The percentage of BODIPY-oligodeoxynucleotide or free dye transferred from the aqueous phase to the organic phase is shown in Table II.

TABLE II

| DYE-OLIGO | CONCENTRATED ACETIC ACID | 0.1M HCl | CONCENTRATED PHOSPHORIC ACID | 5M NaCl |
|---|---|---|---|---|
| Dye Alone | 97% | 98% | 97% | 98% |
| Dye-3-mer | 96% | 97% | 96% | 85% |
| Dye-33-mer | 2% | 11% | 5% | 1% |

As compared to the solvent alone, all four additives substantially increased extraction of the dye-3-mer into the organic phase (to essentially the level of the dye alone) without any appreciable increase in extraction of the dye-33-mer. Addition of such additives should be generally applicable, and would be expected to increase extraction of the smaller BODLPY-oligonucleotides as well Further, addition of additives to increase the ionic strength of the aqueous phase would be expected to increase transfer of secondary amplification products to other organic phases as well.

EXAMPLE 2

Oligodeoxynucleotides were synthesized on an Applied Biosystems Inc. DNA synthesizer (Model 380B) and were purified by denaturing gel electrophoresis. An oligodeoxynucleotide signal primer was synthesized for hybridization to nucleotides 985–1010 of the IS6110 element of M. tuberculosis (Thierry, et al. 1990. Nucl. Acids Res. 18, 188). This sequence is within the IS6110 sequence to be amplified (nucleotides 970–1025 of the IS6110 element). The signal primer sequence was as follows:

5'dGC/TCGAGTTGTCTAC
    ATCCGTATGGTGGATAACGTCTTTCA    (SEQ ID NO:2)

The signal primer was 5'-end labeled with BODIPY 558/568 (Molecular Probes, Inc.) as recommended by the manufacturer. The following amplification and bumper primers were also synthesized:

$S_1$ amplification primer (SEQ ID NO:3)

5'dCGATTCCGCTCCAGACTTCTCGGGT
GTACTGAGATCCCCT $S_2$ amplification primer (SEQ ID NO:4)

5'dACCGCATCGAATGCATGTCTCGGGT
AAGGCGTACTCGACC $B_1$ bumper primer (SEQ ID NO:5)

5'dCGCTGAACCGGAT $B_2$ bumper primer (SEQ ID NO:6)

5'dTGGACCCGCCAAC

BsoBI sites are indicated in bold italics and the cleavage site is indicated by the slash in SEQ ID NO:1. The target binding regions are underlined.

Strand Displacement Amplification was performed generally as described by Walker, et al. (1992. *Nucl. Acids Res.*, supra). Samples for amplification were initially prepared as 35 µL of 50 mM $K_2PO_4$ (pH 7.5), 10.7 mM $MgCl_2$, 2 mM each dGTP, dATP, TTP and αthio-dCTP, 0.14 mg/mL bovine serum albumin, 143 nM primer $S_1$, 714 nM primer $S_2$, 57 nM each primers $B_1$ and $B_2$, and 29 nM 5'-BODIPY-labeled signal primer. Varying amounts of *M. tuberculosis* target DNA were then added to each sample in 5 µL aliquots of 10 mM TRIS-HCl (pH 7.9), 10 mM $MgCl_2$, 50 mM NaCl, 1 mM DTT and 500 ng human placental DNA. These 40 µL samples were denatured by heating for 2 min. in a boiling water bath and equilibrated for 3 minutes at 60° C. for primer annealing. BsoBI and a 5'-3' exonuclease deficient form of DNA polymerase from *Bacillus caldotenax* (5'-3' exo⁻Bca, PanVera) were diluted together to 16 units/µL and 0.4 units/µL, respectively, in 10 mM TRIS-HCI (pH 7.9), 10 mM $MgCl_2$, 50 mM NaCl, 1 mM DTT. The enzyme mixture was prepared at room temperature immediately before addition of a 10 µL aliquot to each of the equilibrated 40 µL samples. The final 50 µL reaction mixture contained 35 mM $K_2PO_4$ (pH 7.5), 3 mM TRIS-HCL (pH 7.9), 15 mM NaCl, 0.3 mM DTT, 105 mM $MgCl_2$, 1.4 mM each dGTP, dATP, TTP and αthio-dCTP, 0.1 mg/mL bovine serum albumin, 500 ng human placental DNA, 100 nM primer $S_1$, 500 nM primer $S_2$, 40 nM each primer $B_1$ and $B_2$, 160 units BsoBI (New England BioLabs), 4 units of 5'-3' exo⁻Bca, 20 nM 5'-BODIPY-labeled signal primer and varying amounts of *M. tuberculosis* DNA.

After enzyme addition, the SDA reaction was allowed to proceed for 30 min. at 60° C. and was terminated by addition of 3 µL of 0.5M EDTA. Samples were then diluted with 350 µL of 0.5M NaCl, 10 mM TRIS-HCl (pH 7.4) and extracted with 400 µL of phenol/chloroform/isoamyl alcohol (25:24: 1). The fluorescence intensity of the organic phase was measured at 579 nm after excitation at 556 nm. Fluorescence intensity values for the organic phase for each initial *M. tuberculosis* target level are presented in Table III. Increased fluorescence intensity above background indicates target-specific conversion of the single-stranded signal primer to a double-stranded form which was cleaved by BsoBI, resulting in release and transfer of a BODIPY-labeled dinucleotide to the organic phase. All *M. tuberculosis* levels tested were detectable over the negative control sample which contained no *M. tuberculosis* target DNA. Increasing fluorescence with increasing levels of target demonstrated that the inventive methods can be used for quantitation of target in amplification reactions.

TABLE III

| # *M. tuberculosis* Target Genomes | Organic Phase Fluorescence Intensity |
|---|---|
| 50000 | 100842 |
| 5000 | 91485 |
| 500 | 86334 |
| 0 | 75253 |

EXAMPLE 3

SDA is performed as described by Walker, et al. (1992. *Nucl. Acids Res.*, supra), using the $S_1$, $S_2$, $B_1$ and $B_2$ primers for amplification of the IS6110 sequence disclosed therein. The amplification reaction also includes a 5'-BODIPY-labeled signal primer which is 33 nucleotides in length (5'-dGGAATTCATCCGTATGGTGGATAACGTCTTTCA— SEQ ID NO:7). The 26 nucleotides at the 3'-end of the signal primer (the target binding sequence) will hybridize to the IS6110 target sequence at nucleotide positions 985–1010, between the amplification primers. 5' to the target binding sequence is a recognition site for the restriction endonuclease EcoRI (bold italics). After SDA, EcoRI is added to the amplification reaction and the samples are incubated for at 37° C. for a sufficient time to allow cleavage of the secondary amplification product.

During the SDA reaction, the signal primer is extended by the polymerase to a length of 49 nucleotides. This 49-mer is displaced by extension of the upstream amplification primer. The 3'-end of the 49-mer will hybridize to the 3'-end of the other amplification primer, forming a double-stranded 70-mer after extension by polymerase. The single-stranded EcoRI recognition site at the 5'-end of the signal primer will become cleavable by EcoRI upon formation of the double-stranded 70-mer. EcoRI cleavage of the double-stranded 70-mer will produce a cleavage product which is a 5'-BODIPY-labeled dinucleotide. This dinucleotide is detectable as a secondary amplification product by virtue of the linked dye.

The cleaved secondary amplification product (the BODIPY-labeled dinucleotide) is detected by mixing the aqueous reaction with phenol/chloroform and separating the aqueous and organic phases, e.g., by centrifugation. Fluorescence in the organic phase is then detected, e.g., by fluorescence spectroscopy. An increase in fluorescence transferred to the organic phase after amplification (as compared to an unamplified control) will indicate that the IS6110 target sequence is present and has been amplified. If no increase in fluorescence is detected in the organic phase, the target sequence is not present or is present but has not been amplified.

EXAMPLE 4

The IS6110 target sequence is amplified by PCR with generation of a secondary amplification product as described by P. M. Holland, et al., supra. The amplification primer pair consists of the target binding regions of SEQ ID NO:3 and SEQ ID NO:4, or the amplification primer pair may consist of the target binding regions of the $S_1$ and $S_2$ primers of Walker, et al. (1992. *Nucl. Acids Res.*, supra). The signal primer included in the amplification reaction is labeled at the 5'-end with a lipophilic dye and has a sequence based on the target binding region of SEQ ID NO:2 (which is identical to the target binding region of SEQ ID NO:7). The sequence of the signal primer may include the entire target binding region, but is preferably a segment of the target binding region which is GC-rich at the 5'-end. As the 5'-end of the target binding region of SEQ ID NO:2 and SEQ ID NO:7 begins with the sequence ATCCG, it may be preferable to eliminate the 5'-AT and begin the signal primer sequence with 5'-CCG. Designing a signal primer with a GC-rich region at the 5'-end promotes the production of smaller polymerase cleavage products (mono- and dinucleotides), thereby ensuring that the cleavage product will be sufficiently lipophilic for transfer to the organic phase. Alternatively, the 5' end of the signal primer may comprise a very short nucleotide "tail" which does not hybridize to the target sequence (preferably no more than about 1–3 nucleotides in length) to that the polymerase encounters the preferred "fork" structure without the need to displace hybridized nucleotides in the signal primer.

The IS6110 target sequence is amplified by PCR in the presence of the amplification primers and the signal primer, essentially as described by R. K. Saiki, et al. (1985. *Science* 230, 1350–1354) and K. B. Mullis, et al. (1987. *Methods Enzymol.* 155, 335–350) utilizing the 5'→3' exonuclease activity of Taq DNA polymerase to generate target-amplification specific signal primer cleavage products as described by Holland, et al., supra. After stopping the amplification reaction, an organic solvent is added to the aqueous reaction phase and mixed. The phases are separated (e.g., by centrifugation) and the organic phase is assayed for presence of the dye using methods appropriate for detection of the selected dye. If an increase in the amount of dye transferred to the organic phase as compared to an unamplified control reaction is detected, the target sequence is present and has been amplified. If no increase is detected, the target sequence is not present or is present but has not been amplified.

What is claimed is:

1. A method for detecting amplification of a target sequence comprising:
   a) hybridizing to the target sequence, in an aqueous solution,
      (i) a hydrophilic signal primer comprising nucleotides linked to a lipophilic label, and
      (ii) an amplification primer;
   b) extending the hybridized amplification primer on the target sequence with a polymerase, whereby extension of the amplification primer displaces the signal primer, or a portion thereof, from the target sequence;
   c) cleaving or nicking the displaced signal primer, or the displaced portion thereof, thereby generating a hydrophobic secondary amplification product having fewer nucleotides linked to the lipophilic label than the hydrophilic signal primer;
   d) contacting the aqueous solution with an organic phase whereby the hydrophobic secondary amplification product is extracted into the organic phase;
   e) separating the organic phase from the aqueous solution, and;
   f) detecting the label of the extracted hydrophobic secondary amplification product as an indicator of amplification of the target sequence.

2. The method of claim 1 wherein the displaced signal primer is rendered double-stranded by hybridization and extension of a second amplification primer, and the hydrophobic secondary amplification product is generated by cleaving the double-stranded signal primer with a restriction endonuclease.

3. The method of claim 1 wherein the displaced signal primer is rendered double-stranded by hybridization and extension of a second amplification primer, and the hydrophobic secondary amplification product is generated by nicking the double-stranded signal primer with a restriction endonuclease.

4. The method of claim 1 wherein the hydrophobic secondary amplification product is generated by cleaving the displaced signal primer, or the displaced portion thereof, with an exonuclease.

5. The method of claim 4 wherein the exonuclease is the polymerase.

6. The method of claim 5 wherein the target sequence is amplified by Polymerase Chain Reaction.

7. The method of claim 1 wherein the lipophilic label is a colorimetric dye.

8. The method of claim 7 wherein the label of the hydrophobic secondary amplification product is detected by spectrophotometry.

9. The method of claim 1 wherein the lipophilic label is a fluorescent dye.

10. The method of claim 9 wherein the fluorescent dye is a BODIPY dye.

11. The method of claim 10 wherein the label of the hydrophobic secondary amplification product is detected by fluorescence spectroscopy.

12. The method of claim 1 wherein the hydrophobic secondary amplification product is extracted by contacting the aqueous solution with phenol/chloroform.

13. The method of claim 1 wherein the aqueous solution further comprises a compound which increases the ionic strength of the aqueous solution.

14. The method of claim 13 wherein the hydrophobic secondary amplification product is extracted by mixing the aqueous solution with the organic phase and separating the organic phase from the aqueous solution.

15. The method of claim 13 wherein the compound which increases the ionic strength of the aqueous solution is selected from the group consisting of mineral acids, organic acids and salts.

16. The method of claim 15 wherein the compound which increases the ionic strength of the aqueous solution is selected from the group consisting of acetic acid, phosphoric acid, hydrochloric acid and sodium chloride.

17. The method of claim 1 wherein the hydrophobic secondary amplification product is transferred to the organic phase by mixing the aqueous solution with the organic phase and separating the organic phase from the aqueous phase.

18. The method of claim 1 wherein the target sequence is amplified by Strand Displacement Amplification.

19. The method of claim 1 wherein the target sequence is amplified by Polymerase Chain Reaction.

20. The method of claim 1 wherein the target sequence is amplified by Self-Sustained Sequence Replication (3SR).

* * * * *